Figure 16:
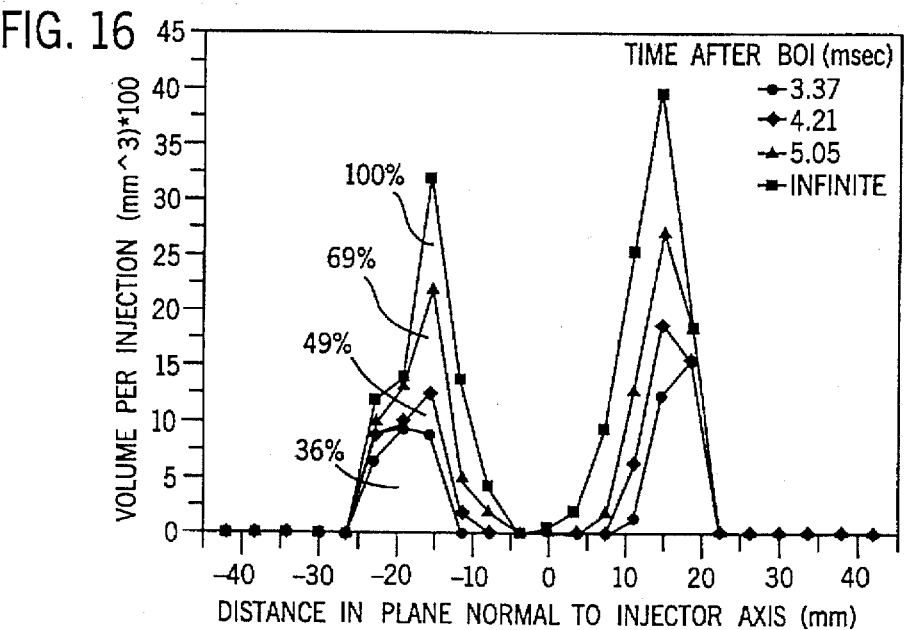

United States Patent [19]

Hoffman et al.

[11] Patent Number: 5,686,989
[45] Date of Patent: Nov. 11, 1997

[54] TRANSIENT SPRAY PATTERNATOR

[75] Inventors: Jeffrey Alan Hoffman; Jay King Martin, both of Madison, Wis.

[73] Assignee: Wisconsin Alumni Research Foundation, Madison, Wis.

[21] Appl. No.: 651,159

[22] Filed: May 17, 1996

[51] Int. Cl.$^6$ .................................................. G01N 15/02
[52] U.S. Cl. .............................. 356/336; 73/1 H; 73/36; 73/37; 73/861
[58] Field of Search .............................. 356/336; 73/16, 73/1 H, 36, 37, 37.5, 53.04, 54.11–54.14, 61.48, 61.69, 64.43, 64.44–64.47, 119 A, 861.61, 864.21, 865.1–865.9; 239/223–224, 382, 383, 389, 393–395, 482, 494–497, 533.2, 533.1, DIG. 1; 72/53

[56] References Cited

U.S. PATENT DOCUMENTS

| | | | |
|---|---|---|---|
| 4,165,635 | 8/1979 | Komaroff et al. | 73/119 |
| 4,413,534 | 11/1983 | Tomoff et al. | 73/864 |
| 4,845,979 | 7/1989 | Farenden et al. | 73/119 |
| 5,000,043 | 3/1991 | Bunch, Jr. et al. | 73/119 |
| 5,212,976 | 5/1993 | Company | 72/53 |
| 5,226,331 | 7/1993 | Thompson et al. | 73/865 |

OTHER PUBLICATIONS

Kashimwaya et al, "The Effect of Atomization of Fuel Injectors on Engine Performance", SAE Techanical Paper Series, No. 900261, Feb. 26–Mar. 2, 1990, pp. 29–35.

Emerson et al, "Structure of Sprays from Fuel Injectors Part III: The Ford Air–Assisted Fuel Injector", SAE Techanical Paper Series, No. 900478, International Congress and Exposition, Detroit, Michigan, Feb. 26–Mar. 2, 1990, pp. 1–15.

MacInnes et al, "Computation of the Spray from an Air–Assisted Fuel Injector", SAE Technical Paper Series, No. 902079, International Fuels and Lubricants Meeting and Exposition, Tulsa, Oklahoma, Oct. 22–25, 1990, 1–19.

Schechter et al, "Air–Forced Fuel Injection System for 2–Stroke D.I. Gasoline Engine", SAE Technical Paper Series, No. 910664, International Congress and Exposition, Detroit, Michigan, Feb. 25–Mar. 1, 1991, pp. 1–21.

Huang et al, "Study of a Small Two–Stroke Engine with Low–Pressure Air–Assisted Direct Injection System", SAE Technical Paper Series, No. 912350, International Fuels and Lubricants Meeting and Exposition, Toronto, Canada, Oct. 7–10, 1991, pp. 1–9.

El–Beshbeeshy et al, "Image Analysis of Diesel Sprays", SAE Technical Paper Series, No. 921628, International Off–Highway & Powerplant Congress & Exposition, Milwaukee, Wisconsin, Sep. 14–17, 1992, pp. 21–34.

(List continued on next page.)

*Primary Examiner*—Frank G. Font
*Assistant Examiner*—Michael P. Stafira
*Attorney, Agent, or Firm*—Andrus, Sceales, Starke & Sawall

[57] ABSTRACT

A measuring device for determining average mass flux, penetration rate, and droplet size both spatially and temporarily in a spray pattern from a spray nozzle. The measuring device includes a movable mounting arrangement that securely positions a spray nozzle such that it can emit a spray pattern along a generally vertical axis. A collection means consisting of a series of collection tubes is positioned below the mounting arrangement such that the collection tubes collect a portion of the spray pattern emitted from the spray nozzle. Each collection tube includes a gas relief opening such that the spray droplets can freely enter the collection tubes. A shutter mechanism is movably positioned between the spray nozzle and the collection means. The shutter mechanism is operated in a timed relation to the pulsing of the injector, such that the shutter mechanism selectively isolates a portion of the spray pattern and the only isolated portion of the spray pattern reaches the collection tubes. In this manner, the measuring device can selectively determine the mass flux distribution in a spray pattern a desired amount of time after the start of injection.

39 Claims, 7 Drawing Sheets

OTHER PUBLICATIONS

Ghandhi et al, "Investigation of the Fuel Distribution in a Two Stroke Engine with an Air-Assisted Injector", SAE Technical Paper Series, No. 940394, International Congress and Exposition, Detroit, Michigan, Feb. 28–Mar. 3, 1994, pp. 1–53.

Parrish, "Spray Characteristics of Compound Silicon Micro Machined Port Fuel Injector Orfices", Thesis for the Degree of M.S., Michigan Technological University, 1993, pp. 1–29.

Sato, "Gasoline Direct Injection for a Loop-Scavenged Two-Stroke Cycle Enginee", International Off-Highway & Powerplant Congress & Exposition, Milwaukee, Wisconsin, Sep., 1987, pp. 177–190.

Dantec Newsletter, "Mass Flux Measurement in Sprays with the Dual PDA", vol. 3, No. 2, 1996.

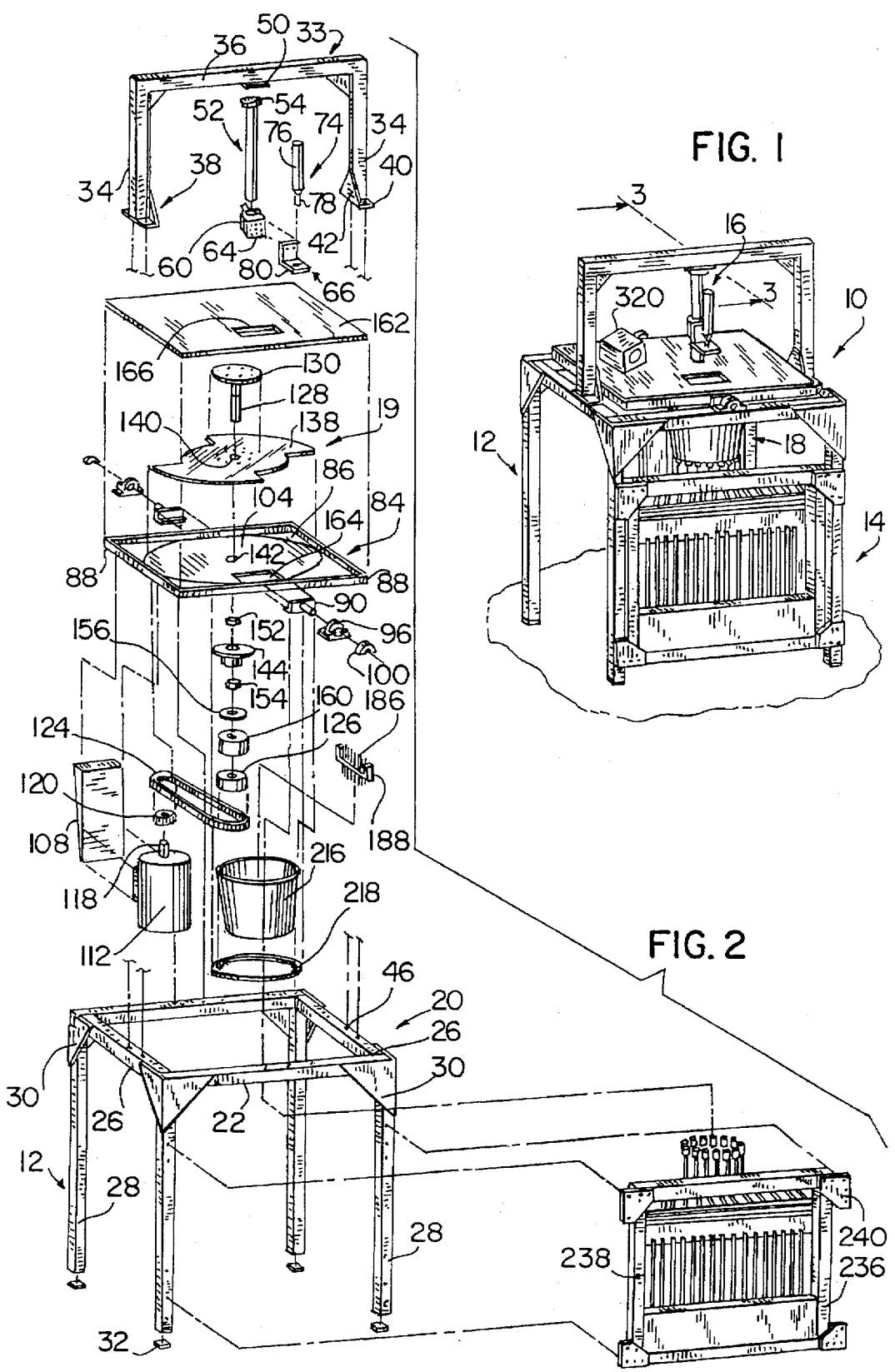

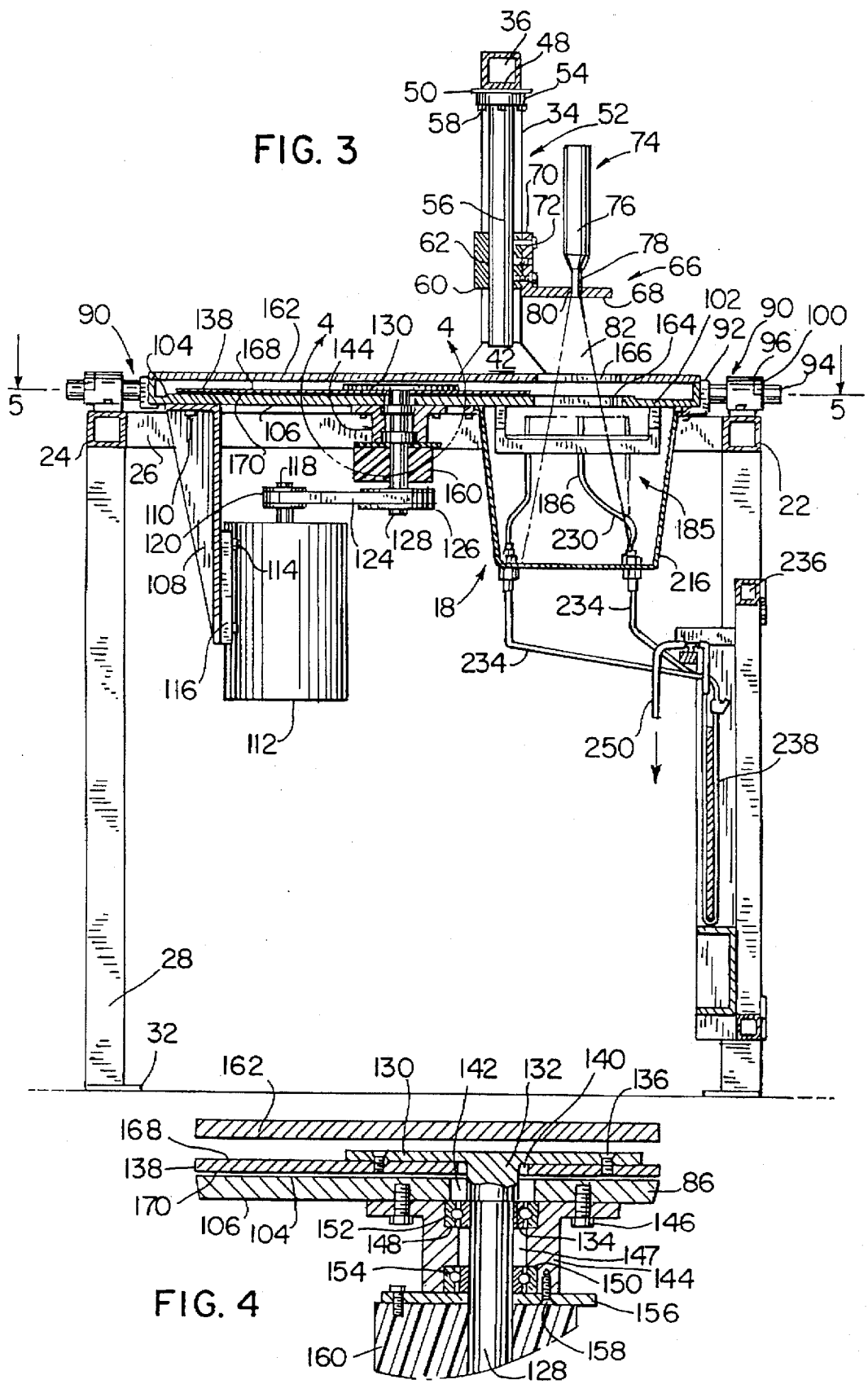

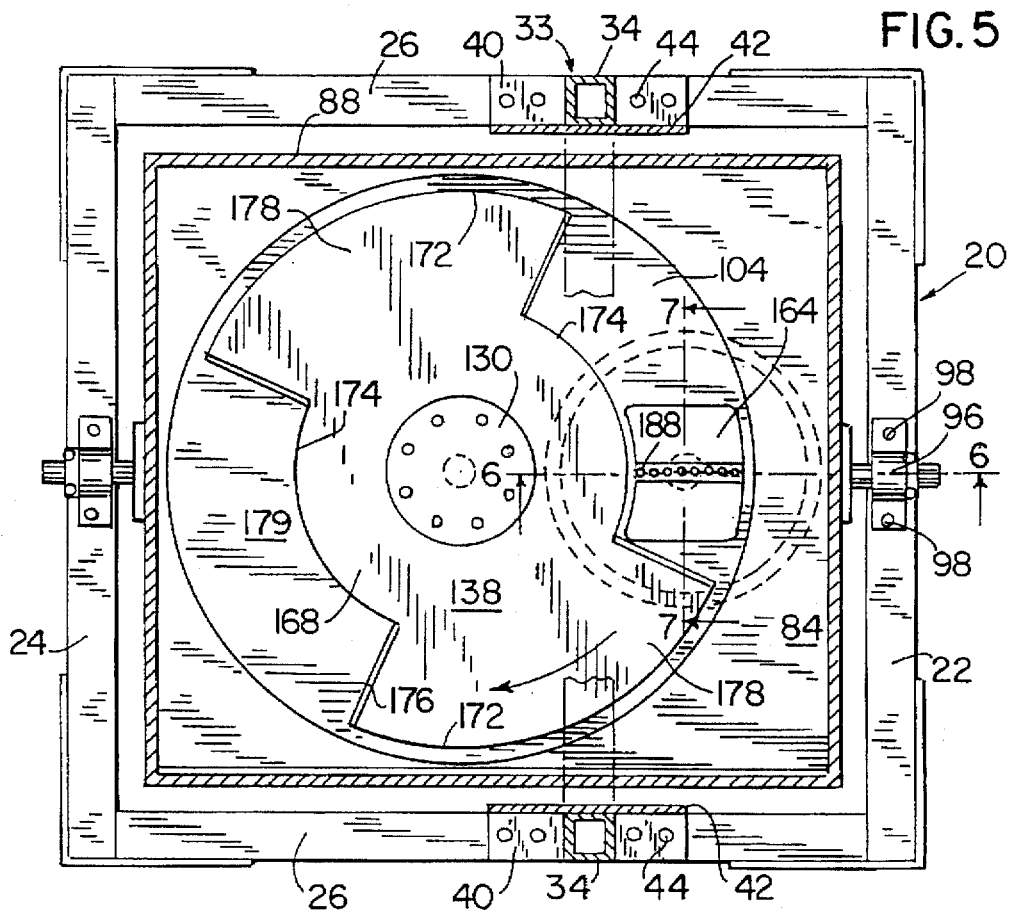
FIG. 5
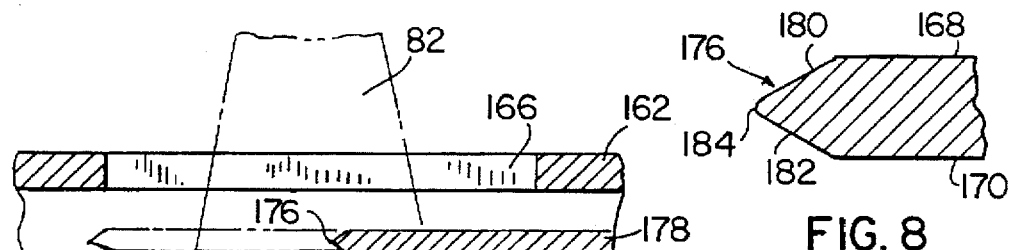
FIG. 7
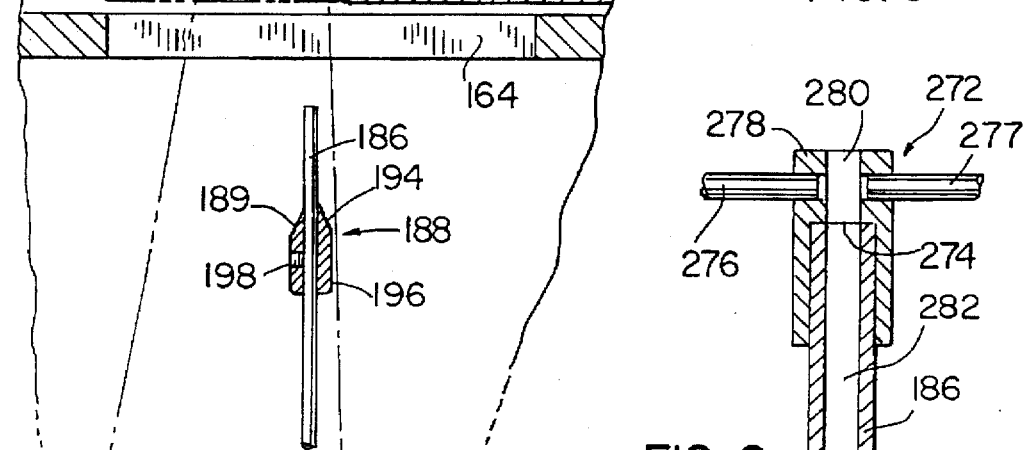
FIG. 8
FIG. 9

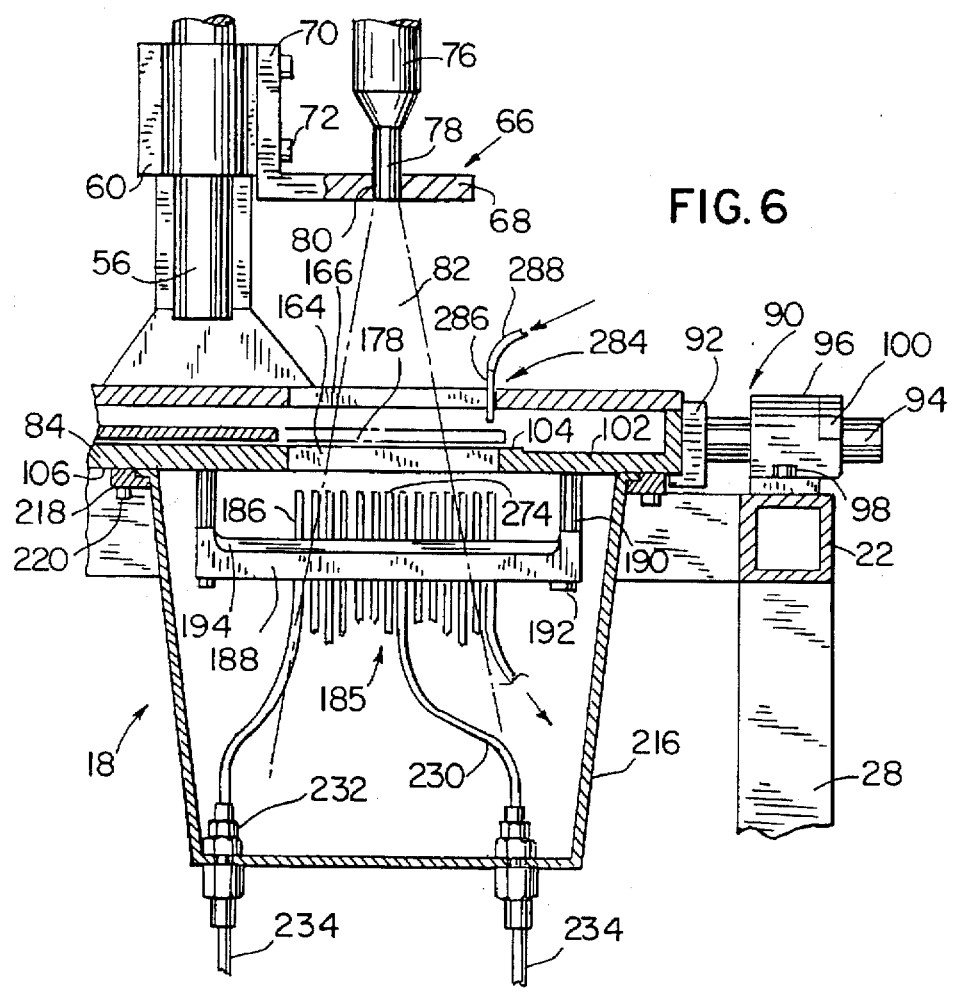
FIG. 6
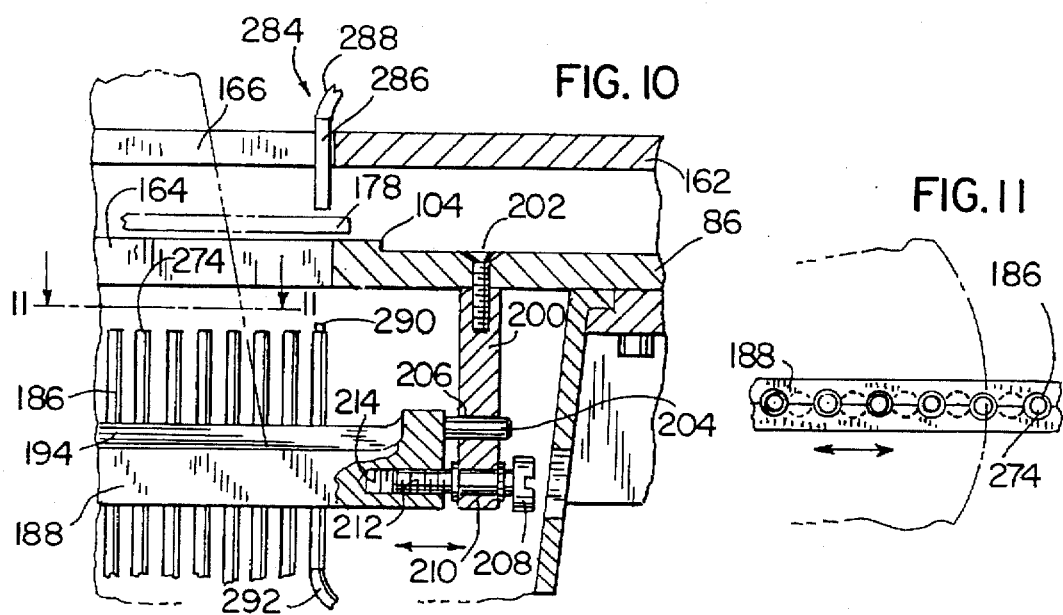
FIG. 10
FIG. 11

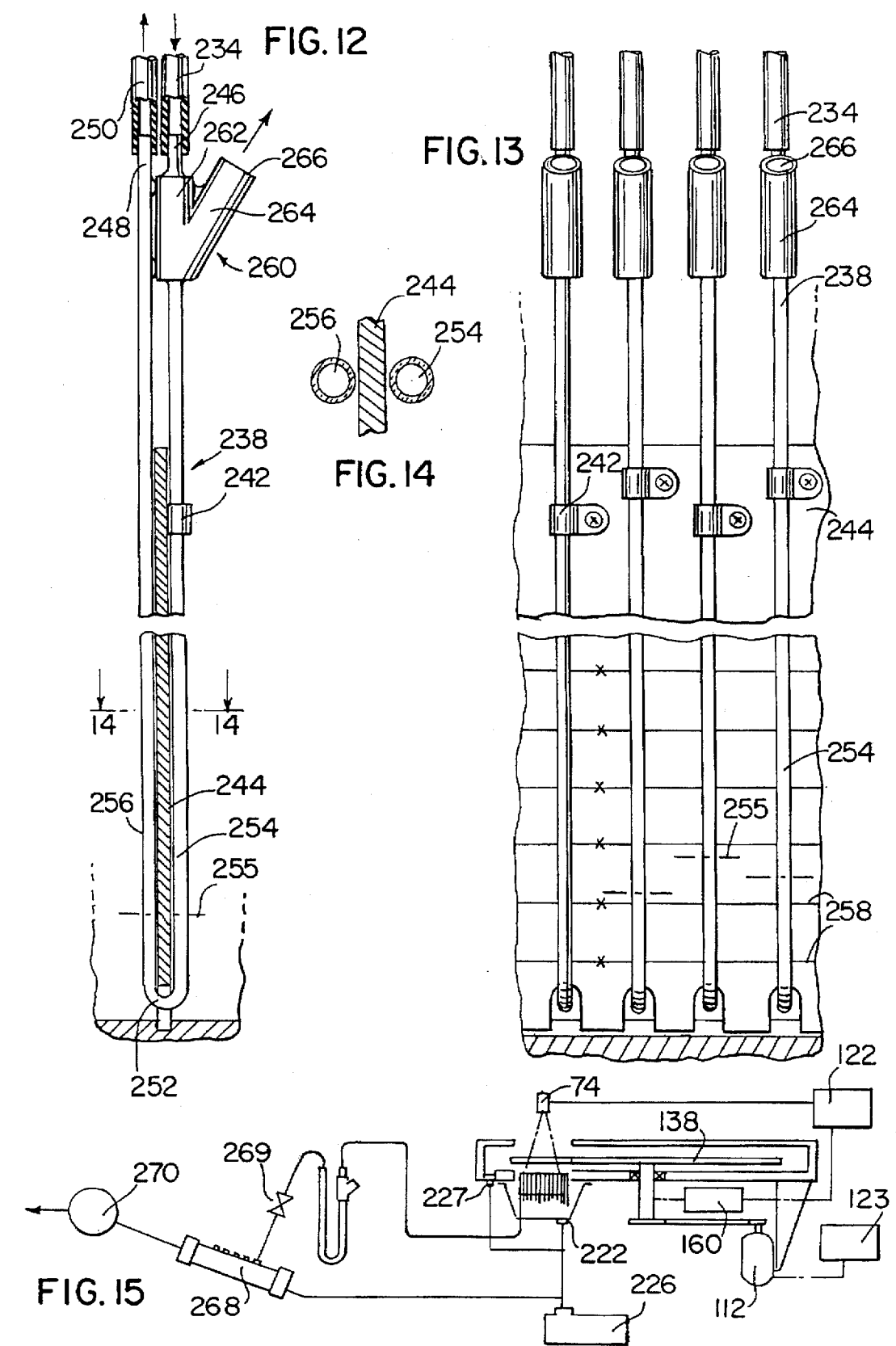

TRANSIENT SPRAY PATTERNATOR

FIELD OF THE INVENTION

The invention relates to a patternator for measuring the output of a spray nozzle. More specifically, the invention relates to a patternator which is able to measure the spray from a nozzle over some fraction of the spray event in order to obtain mass flux data, penetration rates, droplet size and distributions spatially and temporarily within the spray pattern.

BACKGROUND OF THE INVENTION

In testing and constructing spray nozzles, it is important to know the mass flux, penetration rates, droplet sizes and distributions as a function of the position within the spray pattern and with respect to the time after the spray has been released. However, technical difficulties arise when one tries to make such a detailed measurement of a spray. Currently, a number of methods are used to characterize sprays as discussed below.

The first type of spray measurement is called Phase/Doppler Anemometry (PDA). In a PDA measurement, as a spherical particle passes through the intersection of two laser beams, a far field interference fringe pattern is created moving at the Doppler frequency. This information can be collected and processed to give a measurement of both the particle velocity and the particle size.

The second type of spray measurement device is a photograph. Photographs are commonly used for determining standard characteristics of the spray, such as the spray penetration velocity and the spray angle. To make these measurements, a high intensity light source is pulsed at an appropriate instant to expose high speed film to the shadowed spray image. The backlit photograph is basically a single frame showing the spray at a particular instant in time. By analyzing the photograph, the above identified measurements can be determined.

A common type of spray analysis determines the time averaged mass flux of the spray. This technique utilizes a honeycomb structure that collects the spray in individual closed end tubes positioned throughout a given cross-section. After operating the injector or spray nozzle for a period of time, the rate of change of the levels in each of the measurement tubes will correspond to the mass flux at that point in the cross-section.

A specific problem with the time averaged mass flux patternator has to do with the construction of the collection tubes. Each of the collection tubes typically has a closed end to collect the sprayed liquid during spray sampling. The closed-end collection tube creates a stagnation zone at the opening of the collection tube. Since the tubes are closed, gas pressure developed within the tube tends to deflect the spray particles away from the tube opening. The typical mass flux patternator is therefore subject to inaccurate measurements due to the spray being deflected away from the collection tubes.

While the methods listed above provide useful information which make them valuable in characterizing sprays, none of these methods can fully define a spray. Consequently, a new test system which has the capability of transient mass flux measurements, penetration rates, droplet size and distributions both spatially and temporarily within a spray pattern would yield information not supplied by current techniques and would be desirable and greatly useful in analyzing the characteristics of a given spray.

SUMMARY OF THE INVENTION

The invention is a device and method for measuring the mass flux distribution, penetration rates, droplet sizing and distributions within either a steady state or transient spray pattern.

The measuring device includes an injector mounting system which securely positions the injector to be tested. The injector mounting system allows the position of the injector to be adjusted relative to an otherwise fixed platform, such that the amount of spray at various distances from the spray nozzle can be measured.

A collection means is mounted to a stationary frame below the injector. The collection means is positioned such that it collects a portion of the spray emitted from the injector spray nozzle at a predetermined distance therefrom. The collection means collects the spray and accumulates the spray such that the amount of mass flux in specific portions of the spray can be determined.

In a preferred embodiment of the invention, the collection means consists of an array of collection tubes mounted in a single row that is normal to the spray axis passing through the injector. Preferably, each of the collection tubes contains a gas relief opening positioned between the open mouth of the tube and the collection reservoir. The gas relief opening acts to minimize the stagnation zone which normally develops at the opening of a closed ended tube. The gas relief opening thereby allows the particles of spray to freely enter the collection tubes without encountering any stagnation zone.

A shutter mechanism is positioned below the injector nozzle and above the collection means. In the preferred embodiment, the shutter mechanism is a disk mounted to a rotating shaft. The disk contains a pair of open sections separated by a pair of shutters along the outer circumference of the disk. Preferably, the shutters and the open areas are of equal size, such that the rotating disk is balanced when rotated at high speed.

An encoder is mounted on the rotating shaft of the shutter mechanism to provide an electronic indication of the position of the shutter contained on the rotating disk. Preferably, the encoder provides an electronic signal corresponding to each degree of rotation of the disk.

A controller is connected to both the shaft encoder and the injector, such that the controller can operate the injector at a specified time corresponding to the position of the rotating disk. In this manner, the injector can be operated by the controller such that the leading edge of the shutter contained on the rotating disk slices through the spray pattern from the injector and isolates only a portion of the spray which reaches the collection means to be measured.

The method of measuring the mass flux distribution of a spray pattern from an injector having a spray nozzle consists first of positioning an injector on a movable platform at a predetermined distance above a stationary spray collection means. With the injector and collection means in place, a shutter mechanism is used to isolate the desired portion of the spray pattern which reaches the collection means. This method is accomplished by first pulsing the injector and thereafter passing the shutter mechanism through the emitted spray pattern at high speed a specified amount of time after the start of the injection. In this manner, only a portion of the spray pattern reaches the collection means, while the remaining amount of spray is blocked by the shutter.

After the measurements are taken from the collection means following the series of injector firings, the injector can be moved either closer to or further from the collection means such that the shutter mechanism will then isolate a larger or smaller section of the spray pattern. Again, measurements are taken from the collection means. Thereafter, the position of the injector is again adjusted. This process is repeated for a range of injector-to-collection distances. Additionally, the timing of the beginning of injection may be altered with respect to the shutter position. The combination of the measurements taken provide measurements of the mass flux distribution, penetration rates, droplet sizing and distribution within the spray pattern.

In the preferred embodiment of the invention, the shutter mechanism is a continuously rotating disk having alternating open and blocking sections. A shaft encoder provides an electronic signal corresponding to the position of the blocking section of the disk, referred to herein as the shutter. The controller receives the signal from the encoder and can then operate the injector at a specified time corresponding to the position of the shutter, such that the shutter intersects the spray pattern a selected period of time after the start of injection.

In the preferred embodiment of the invention, a series of laser discriminators are positioned across the open mouth of each collection tube to determine the size and velocity of the spray particles entering each of the tubes.

In the preferred embodiment of the invention, a AC motor operates to rotate the disk and the connected encoder shaft at a constant speed.

BRIEF DESCRIPTION OF THE DRAWINGS

The drawings illustrate the best mode presently contemplated of carrying out the invention.

In the drawings:

FIG. 1 an isometric view of a transient spray patternator in accordance with the invention for measuring the mass flux distribution in a spray pattern from an injector having a spray nozzle;

FIG. 2 is an exploded view of the apparatus shown in FIG. 1;

FIG. 3 is a sectional view taken along 3—3 of FIG. 1;

FIG. 4 is a magnified view of the area indicated by line 4—4 in FIG. 3;

FIG. 5 is a top partial sectional view taken along line 5—5 in FIG. 3;

FIG. 6 is a partial sectional view taken along line 6—6 in FIG. 5;

FIG. 7 is a partial sectional view taken along line 7—7 in FIG. 5 showing the position of the movable shutter and the collection tubes in relation to the spray pattern;

FIG. 8 is a detailed cross-sectional view of the leading edge of the shutter of the present invention;

FIG. 9 is a detailed cross-section view showing the laser discriminator positioned across the sampling tube of the present invention;

FIG. 10 is a detailed cross-sectional view showing the movable mounting arrangement of the collection tube holder;

FIG. 11 is a detailed top view taken along line 11—11 of FIG. 10, showing the translational movement of the series of collection tubes;

FIG. 12 is a side elevation view of a collection tube of the invention;

FIG. 13 is a partial front elevation view of a series of collection tubes according to the invention;

FIG. 14 is a sectional view taken along line 14—14 of FIG. 12;

FIG. 15 is a schematic view of an overall system including the patternator of FIG. 1 for measuring the mass flux distribution in a spray pattern from an injector having a spray nozzle;

FIG. 16 is a sample graph showing the spray distribution in relation to the injection axis at a series of times after the beginning of injection for a given plane below the injector;

FIG. 17 is a sample graphic display of the average liquid mass flux contours a specific time after the beginning of injection; and FIG. 18 is a timing diagram showing the signal from the shaft encoder, the injector firing signal, and the laser discriminator output, and the shutter position indicating signal.

DETAILED DESCRIPTION OF THE DRAWINGS

The entire device for measuring the mass flux distribution in a spray pattern from an injector having a spray nozzle, which is the subject of the present invention, is illustrated in FIG. 1 and is generally designated by reference numeral 10. The measuring device 10, hereinafter alternately referred to as the patternator, is generally comprised of a mounting frame 12, a measuring section 14, an injector mounting arrangement 16, a collection system 18 and a shutter mechanism 19.

The mounting frame 12 contains a horizontally disposed rectangular support frame 20 consisting of a front rail 22, a back rail 24, and a pair of side rails 26. In the preferred construction of the mounting frame 12, each of the rails contained in the support frame 20 is a hollow metallic tube having a square cross-section, as can best be seen in FIG. 3. The support frame 20 is spaced above a floor surface by a series of vertical legs 28. Each of the vertical legs 28 is securely joined to the support frame 20 at a corner of the rectangular support frame 20.

In the preferred embodiment of the invention, the vertical legs 28 are hollow metallic tubes having a square cross-section. A series of corner supports 30 are securely connected between the support frame 20 and each of the vertical legs 28 to provide additional support for the mounting frame 12. Contained on the lower end of each of the vertical legs 28 is a rectangular pad or foot 32 which provides additional support for the mounting frame 12.

The injector mounting arrangement 16 contains an overhead U-shaped support 33 which is comprised of a pair of vertical arms 34 securely joined to a horizontal support arm 26. As can best be seen in FIGS. 3 and 5, each of the vertical support arms 24 and the horizontal support arm 26 are constructed of hollow metal tubing having a square cross-section. A mounting bracket 38 is securely attached to the lower end of each of the vertical support arms 34. The mounting bracket 38 is comprised of a horizontally disposed flange 40 and a vertically disposed support member 42. The horizontally disposed flange 40 contains a series of mounting holes 44. A series of connectors (not shown), such as screws or bolts, pass through the mounting holes 44 and are received in a series of matching receiving holes 46 contained in the side rails 26 of the mounting frame 12 to securely attach the vertical arms 34 to the support frame 20. The vertical support member 42 of the mounting bracket 38 extends upward from the inside edge of the flange 40 and is securely connected to the inside face of the vertical arm 34. The support member 42 thereby provides additional support for the vertical arms 34.

Securely connected to the bottom wall 48 of the horizontal support arm 36 is a mounting plate 50, as can be seen in FIG. 3. Mounting plate 50 is a planar element having a width larger than the horizontal support arm 36 and contains a series of mounting holes (not shown) which provides a point of connection between the horizontal support arm 36 and the injector support structure 52.

The injector support structure 52 consists of a mounting head 54 securely connected to an injector shaft 56. The mounting head 54 of the injector support 52 is securely connected to the mounting plate 50 through a series of connectors, such as bolts 58, which are received by the mounting holes in the mounting plate 50. As shown in FIG. 3, the injector shaft 56 extends along a vertically disposed longitudinal axis which is perpendicular to the support frame 20.

A vertical adjustment bracket 60 is mounted to the injector shaft 56. The vertical adjustment bracket 60 contains a vertically disposed flat face surface 64 and a shaft opening 62 which is sized to slidably engage the outer diameter of the injector shaft 56. Connected to the flat face surface 64 of the vertical adjustment bracket 60 is an L-shaped injector mounting platform 66, as can best be seen in FIGS. 3 and 6. The injector mounting platform 66 is comprised of a horizontally disposed injector mounting plate 68 and a vertical connection plate 70. A series of connectors 72 pass through the connection plate 70 to securely join the injector platform 66 to the adjustment bracket 60.

A generic injector is shown in the figures by reference numeral 74. Although the injector 74 is referred to as an injector throughout the following description, the injector 74 could be replaced by a pressurized atomizer or similar structure and the measuring device 10 would operate in an identical fashion.

The injector 74 is comprised of an injector body 76 and a spray nozzle 78. Although not shown in the Figures, the injector body 76 is connected to a source of liquid to be sprayed during testing. The injector 74 is securely mounted to an injector platform 66 having an opening 80 such that the spray nozzle 78 passes through the injector opening 80 contained in the injector platform 66. As shown in the figures, the injector 74 is mounted such that the spray pattern 82, as shown by the broken lines in FIGS. 3 and 6, is centered about a substantially vertical spray axis passing through the center of spray nozzle 78 and injector body 76. The injector platform 66 is constructed such that a variety of injectors 74 can be mounted thereto, allowing the measuring device 10 of the invention to be used to determine the mass flux distribution from a variety of injector spray nozzle designs.

As can best be seen in FIGS. 3 and 6, the vertical adjustment bracket 60 and the attached injector platform 66 can be moved vertically along the injector shaft 56 as shown by the arrows in FIG. 6. Additionally, the injector body 76 can be rotated within the injector platform 66. The movement of the vertical adjustment bracket 60 along the injector shaft 56 moves the injector 74 parallel to the vertical injector spray axis. This movement of the vertical adjustment bracket 60 varies the spacing between the spray nozzle 78 and the stationary support frame 20, the significance of which will be discussed in greater detail below.

Referring again to FIG. 2, a base 84 is pivotally connected to the front rail 22 and the back rail 24 of the mounting frame 12. The base 84 is preferably a rectangular tray-like structure having a bottom wall 86 connected along its outer edges to four side walls 88 which extend upward therefrom. A pair of pivot elements 90 are attached to both the front and back side walls 88 of the base 84. Referring to FIG. 3, each of the pivot elements 90 consists of an attachment head 92 securely joined to a pivot rod 94. Each attachment head 92 is securely attached to the bottom wall 86 of the base 84 with its rod 94 projecting outwardly therefrom. Each pivot rod 94 passes through a pillow block 96, one of which is attached to the front rail 22 and another of which is attached to the back rail 24. As can best be seen in FIG. 5, a pair of connectors 98 securely attach pillow blocks 96 to the front rail 22 and the back rail 24. A lock 100 is attached to the pillow block 96 to securely hold pivot rod 94, and corresponding base 84, in a fixed position when desired. As best shown in FIGS. 3 and 5, the pair of pivot elements 90 position the base 84 within the inside edge and slightly above the support frame 20.

Referring to FIG. 3, the upper internal surface 102 of the bottom wall 86 of base 84 has a raised circular shutter platform 104 integrally formed thereon. The diameter of the shutter platform 104 is slightly less than the width of the base 84 between the pair of lateral side walls 88 and is slightly offset from the center of the base 84, as can best be seen in FIG. 5.

Securely connected to the lower external surface 106 of the base 84 is a motor mounting bracket 108. The motor mounting bracket 108 is securely connected to the base 84 by a series of connectors 110, such as bolts or screws. A driving motor 112 is securely connected to the motor mounting bracket 108 by a series of connectors 114, such as bolts or screws, which pass through a mounting plate 116 securely connected to the driving motor 112. In the preferred embodiment of the invention, the driving motor 112 is a ¾ horsepower, 3-phase DC motor, although any motor which produces a constant controllable speed could be used. A drive shaft 118 extends upward from the driving motor 112 and contains a securely mounted drive wheel 120. The driving motor 112 is coupled to a motor controller which is symbolically shown as controller 123, in FIG. 15.

The drive wheel 120 is coupled via a belt 124 and a tooth wheel 126 to a disk shaft 128. The disk shaft 128 is connected to a circular disk mounting plate 130. As can best be seen in FIG. 4, the disk mounting plate 130 contains a hub 132 which is used to securely attach the disk mounting plate 130 to the rotating disk shaft 128. In the preferred embodiment of the invention, the disk shaft 128, the hub 132, and the disk mounting plate 130 are a unitary structure. The outer diameter of the hub 132 is slightly larger than the outer diameter of the disk shaft 128, which creates an annular flange 134.

A series of connectors 136, such as screws, are used to connect a disk 138 to the lower surface of the disk mounting plate 133. The hub 132 of the disk mounting plate 130 passes through a shaft aperture 140 contained at the axial center of the disk 138. The hub 132 further passes through a shaft aperture 142 contained at the axial center of a shutter platform 104.

A bearing housing 144 is connected to the lower external surface 106 of the bottom wall 86 of the base 84 by a series of connectors 146, such as screws. Bearing housing 144 is positioned such that the central bearing aperture 147 is axially aligned with the shaft aperture 142 contained in the base 84. The bearing housing 144 contains an upper bearing seat 148 and a lower bearing seat 150. An upper bearing 152 is mounted in the upper bearing seat 148 while a lower bearing 154 is mounted in the lower bearing seat 150. The upper bearing 152 and the lower bearing 154 permit the disk shaft 128 to rotate within the bearing housing 144.

As can best be seen in FIG. 4, the annular flange 134 contained on the hub 132 of the disk mounting plate 130 contacts the upper bearing 152, which is therefore securely positioned between the lower external surface 106 of the bottom wall 86 of the base 84 and the upper bearing seat 148. The height of shaft mounting portion 132 provides the proper spacing between the disk 138 and the shutter platform 104 of the base 84 such that the disk 138 can freely rotate about the shutter platform 104. A cap 156 is securely connected to the lower edge of the bearing housing 144 by a series of connectors 158 to securely hold the lower bearing 150 within the bearing housing 144.

Connected to the lower surface of the cap 156 is a shaft encoder 160. The shaft encoder 160 is connected to the controller 122 to provide an electronic signal indicating the rotational position of the disk shaft 128 and the disk 138 connected thereto. The shaft encoder 160 is a well known device in the automotive field and a detailed discussion thereof will be omitted. Although the measuring device 10 is described as having a shaft encoder 160, any similar device which provides an indication of the position of a rotating shaft could be used.

A cover 162 is attached to the upper edge surfaces of each side wall 88 of the tray-like base 84 as shown in FIG. 3. In the preferred embodiment of the invention, the cover 162 is a clear sheet of plastic. The cover 162 functions to retain the spray within the base 162 when the disk 138 is spinning, while allowing the user of the measuring device 10 to monitor the operation of the disk 138.

As can be clearly seen in both FIGS. 2 and 3, the base 84 has a spray opening 164 and the cover 162 has a corresponding aligned spray opening 166. As shown in FIG. 6 each of the spray openings 164 and 166 are directly aligned, such that the spray 82 can freely pass through both the cover 162 and the bottom wall 86 of the base 84.

The shutter mechanism 19 of the invention is preferably comprised of the rotatable disk 138, the motor 112, and the disk shaft 128. Referring now to FIGS. 3 and 5, the circular disk 138 has a flat top face 168 and a corresponding flat bottom face 170 spaced from the upper surface 168 by the overall uniform thickness of the circular disk 138. The outer circumference of the disk 138 is defined by a pair of outer arcuate edges 172 and a pair of inner arcuate edges 174. Each of the outer edges 172 is connected to an adjacent inner edge 174 by one of four generally radially extending leading edges 176.

A pair of spaced shutters 178 is contained on the disk 138. The shutters 178 are defined as the solid blocking section or area of the disk 138 which is positioned between a pair of leading edges 176. The width of each shutter 178 is defined as the radial distance between the arc of the outer radiused edge 172 and the arc of the inner radiused edge 174. In addition to the pair of shutters 178, the disk 138 contains a pair of open areas 179 which extend between a pair of leading edges 176. In the preferred embodiment, the open areas 179 are of equal arcuate length to the pair of shutters 178. As can be seen in FIG. 5, the length of each outer radiused edge 172 is equal to the outer radiused edge contained on the opposite side of the disk 138. Additionally, each of the inner radiused edges 174 are equal in length, such that the disk 138 is completely balanced.

Turning now to FIG. 8, the leading edges 176 are preferably comprised of an upper tapered surface 180 and a lower tapered surface 182 which meet at a cutting edge 184. The length of the upper tapered surface 180 and the length of the lower tapered surface 182 are equal, and the angle between the upper tapered surface 180 and the top surface 168 is equal to the angle between the lower tapered surface 182 and the bottom surface 170. Thus, when the disk 138 is rotated, the leading edge 176 causes air or spray to be equally directed over the upper tapered surface 180 and the lower tapered surface 182.

As can be seen in FIG. 5, the width of the spray opening 164 roughly corresponds to the width of the pair of shutters 178. As can be seen in FIG. 6, when the inner edge 174 of disk 138 is aligned with the spray opening 164 such that open area 179 of disk 138 overlies opening 164, the entire spray 82 can freely pass through the spray opening 164. Likewise, when the outer edge 172 of disk 138 is aligned with the spray opening 164, such that shutter 178 of disk 138 overlies opening 164, as shown by the phantom lines in FIG. 7, the entire spray contacts the shutter 178 and is blocked or prevented from passing through the spray opening 164.

The collection system 18 of the patternator 10 is most clearly shown in FIG. 6. The collection system 18 contains a series of spaced collection tubes generally referred to at 185. The collection tubes 185 consist of a series of sampling tubes 186 positioned below the bottom wall 86 of the base 84. The series of sampling tubes 186 are securely held in a straight line by a tube holder 188, as shown best in FIG. 5. The tube holder 188 has a longitudinal length which is horizontally disposed and perpendicular to the vertical spray axis passing through the injector 74. The tube holder 188 is connected to a pair of mounting legs 190 to securely position the tube holder a desired distance below the external surface 106 of the base 84. A pair of connectors 192 pass through the tube holder 188 and the mounting legs 190 to engage the base 84.

As shown in FIG. 5, the tube holder 188 is positioned such that it bisects the length of the spray opening 164. As previously stated, the tube holder 188 is positioned such that it is normal to the spray axis passing through the injector 74. As best seen in FIG. 7, the tube holder 188 contains a pair of beveled top edges 194 which angle downward from the point of contact with the sample tubes 186 to opposite planar side walls 196. A threaded opening 198 is aligned with each tube opening 189 contained in the tube holder 188. The threaded opening 198 receives an externally threaded connector (not shown) to securely position the sampling tube 186 in the tube holder 188.

Shown in FIG. 10 is an alternate translating mounting arrangement for the tube holder 188. In this embodiment, a vertical mounting leg 200 is attached to the base 86 by a connector 202, such as a screw. A peg 204 is connected to the tube holder 188 and is received by an aperture 206 contained in the mounting leg 200. An adjustment mechanism, such as the screw 208, passes through a second opening 210 contained in the mounting leg 200. The threaded shaft 212 of the screw 208 is received by an internally threaded bore 214 contained in the tube holder 188. By rotating the screw 208, the tube holder 188 can be moved in a direction parallel to its longitudinal length, such that the position of the individual sampling tubes 186 can be dithered as shown in FIG. 11. The position of each sampling tube 186 can be adjusted, such that each sampling tube 186 can be moved to the position shown by the phantom lines in FIG. 11. By adjusting the sampling tubes 186 in a radial direction as shown, a more detailed view of the spray pattern 82 can be obtained.

Referring again to FIG. 6, a collection pail 216 is positioned to completely surround the tube holder 188 and the series of sampling tubes 186. The pail 216 is securely connected to the underside of base 84 by a pail flange 218 and a series of connectors 220. The pail 216 is positioned such that the liquid contained in the spray pattern 82 which is not received by the series of sampling tubes 186 is captured within the pale 216. The pail 216 contains a drain 222 (FIG. 15). The drain 222 allows liquid collected on the bottom of the pail 216 to flow into an external collector 226. Additionally, the base 84 also includes a drain 227 which also flows into the external collector 226.

Referring again to FIG. 6, each of the sampling tubes 186 is connected at its lower end to a flexible tube 230 (only two connections are actually illustrated however). Each flexible tube 230 is connected to a corresponding coupling 232 which passes through the bottom wall of the pail 216. Connected to the external end of the coupling 232 is a connecting tube 234. The coupling 232 provides a liquid-tight connection between the flexible tube 230 and the connecting tube 234 through the wall of the pail 216.

As can be seen in FIG. 3, each of the connecting tubes 234 extends between the pail 216 and the measuring section 14 of the patternator. The measuring section 14 is comprised of an exterior frame 236 onto which a series of manometers 238 are mounted. The frame 236 is mounted to the vertical legs 28 of the mounting frame 12 by a series of brackets 240.

Each of the series of manometers 238 is securely connected by a mounting clip 242 to a measurement guide board 244. Measurement guide board 244 is securely connected to the mounting frame 236, such that the series of manometers 238 are securely positioned as shown in FIG. 1.

As shown in FIG. 3, each collection tube 185 is comprised of a sampling tube 186, a flexible tube 230, a coupling 232, a connecting tube 234 and a manometer 238 connected in a liquid-tight manner to allow liquid from the spray to pass from the sampling tube 186 to the manometer 238. The series of manometers 238 are positioned in an order corresponding to the order of the sampling tubes 186 in the tube holder 188.

As shown in FIG. 12, the inlet 246 of each individual manometer 238 is connected to the connecting tube 234. In this manner, the liquid spray from the injector 74 which is received by the sampling tubes 186 is transferred to the manometers 238. The manometer 238 is a generally U-shaped glass tube extending between inlet 246 and outlet end 248. As shown in FIGS. 3 and 12, outlet 248 of each manometer 238 is connected via a tube 250 to a source of atmospheric pressure.

A U-shaped reservoir 252 is positioned in the manometer 238 between the inlet 246 and the outlet 248. As the liquid spray enters the inlet 246 through the connecting tube 234, it travels down the body of the manometer 238 until it reaches the reservoir 252. Liquid is then stored in the reservoir 252 as the injector 74 continues to fire. As the liquid continues to accumulate, the level of liquid travels up the front side 254 and the back side 256 of the U-shaped manometer 238. Since both the inlet 246 and the outlet 248 of the manometer 238 are exposed to atmospheric pressure, the level of liquid in both the front side 254 and the back side 256 will be equal. The level of liquid in the manometer 238 is shown by the dashed line 255 in both FIGS. 12 and 13.

As shown in FIG. 13, a series of measuring lines 258 are contained on the measurement guide board 244, such that as the liquid level rises in each of the manometers 238, the level of liquid can be determined with reference to the measuring lines 258. Since the level of liquid is the same in both the front side 254 and the back side 256, the level of liquid shown by the measuring lines 258 is doubled to determine the actual amount of liquid contained within each of the manometers 238.

Referring now to FIG. 12, a gas separating portion 260 is positioned between the inlet 246 and the reservoir 252 in each manometer 238. The gas separating portion 260 includes an inlet bulb 262 which is a portion of the front side 254 of the collection tube having an increased diameter. Connected to the inlet bulb 262 at an angle of approximately 30° is a hollow gas relief tube 264. The gas relief tube 164 terminates at a gas relief opening 266. The gas relief opening 266 acts as a gas relief valve such that as liquid enters the sampling tube 186 attached to the manometer 238, air can be displaced out of the tube through the gas relief opening 266. In this manner, the stagnation pressure which is normally created at the opening of a closed end tube is minimized. By minimizing the stagnation pressure, the liquid droplets from the spray 82 can freely enter the sampling tubes 186, which results in a more accurate measurement.

In an alternate embodiment of the invention, the gas relief opening 266 could be connected to a source of negative air pressure such that the pressure at the opening of each sampling tube 186 would be less than atmospheric. Reducing the pressure at the opening of the sampling tube 186 would further aid in allowing spray droplets to enter the sampling tubes 186.

Referring now to FIG. 15, the outlet 248 of each manometer 238 can be connected to a vacuum chamber 268 through valve 269. During operation of the measuring device 10, the vacuum chamber 268 is connected to atmospheric pressure and each valve 269 is open, such that the liquid level in the reservoir portion 252 is balanced. After an injector 74 is tested, the vacuum chamber 268 can be connected to a vacuum pump 270, which can be used to remove all of the liquid contained in the manometers 238 and the remaining portions of each collection tube 185. Selectively opening and closing valve 269 can isolate a particular collection tube 185 to be emptied as desired.

Referring now to FIG. 9, in a preferred embodiment each of the sampling tubes 186 can have a particle sizer 272 connected across its open inlet mouth 274. In a preferred embodiment of the invention, the particle sizer 272 consists of a pair of fiber optic cables, supply cable 276 and receptor cable 277, positioned closely above the open mouth 274, within an end cap 278 mounted on the inlet end of tube 186. End cap 278 has an internal opening 280 which corresponds in diameter to the internal passageway 282 contained within each of the sampling tubes 186. The supply fiber optic cable 276 is connected to a laser light source (not shown) and the receptor fiber optic cable 277 is connected to the controller 122.

When no spray is present, laser light travels from the supply cable 276 across the internal opening 280 and is received by the receptor cable 277. As particle droplets enter the internal opening 280, the liquid droplets scatter a portion of the laser light traveling between the supply cable 276 and the receptor cable 277. The result of this reduced amount of light received by the receptor cable 277 will be discussed in greater detail below.

Figure 18:
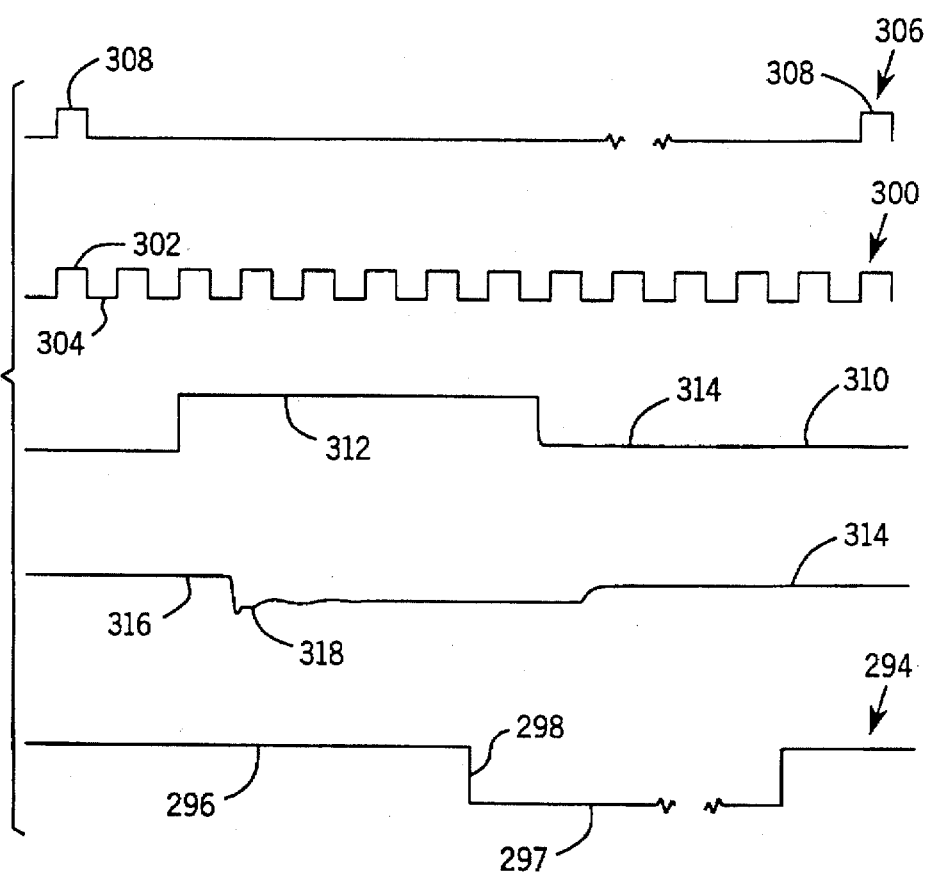

Referring now to FIG. 10, a shutter position indicator 284 is shown in an alternate embodiment of the invention. The shutter position indicator 284 consists of a fiber optic supply cable 288 having a discharge end 286 securely mounted to the cover member 162 along the edge of spray opening 166. The discharge end 286 is connected to a fiber optic supply cable 288 which receives a constant light source, not shown. The light is emitted from the discharge end 286 downward through the spray opening 164 and is received by a receptor 290. The receptor 290 is securely positioned within the outmost sampling tube 186. The receptor 290 is securely connected to a fiber optic cable 292 which is joined to a scope through a photo diode (not shown). The shutter position indicator 284 is useful to determine the precise instant at which the shutter 178 passes over and blocks the sampling tubes 186. When the shutter 186 passes over the collection tubes 186, the solid shutter 178 prevents the light emitted by the discharge end 286 from being received by the receptor 290. The shutter position device 284 generates a shutter signal 294, as shown in FIG. 18. When the shutter 178 travels over and blocks the sampling tubes 186, the signal 294 drops from a high value 296 to a low value 297. The precise instant at which the shutter 178 passes between the discharge end 286 and the receptor 290 is indicated by the leading edge 298. The shutter signal 294 remains at the low value 197 while the shutter 178 is positioned over a series of sampling tubes 186. After the shutter 178 completely passes over the sampling tubes 186, the signal 294 again returns to the high value 296.

The operation of the measuring device 10 will now be discussed. The measuring device 10 is particularly useful in determining the mass flux distribution in a spray pattern from an injector or liquid atomizer of any type. For example, the measuring device 10 could be used to determine the spray characteristics from a paint gun nozzle, or from a fuel injector. The first step in using the patternator 10 is to securely attach an injector 74 to the injector platform 66. As shown in FIGS. 3 and 6, the injector is positioned such that the spray axis of the nozzle 78 is perpendicular to the tube holder 188, and therefore perpendicular to the open mouth portion 274 of each sampling tube 186. Once the injector 174 is in place, the vertical position of the injector platform 66, and therefore the spray nozzle 78, can be adjusted by moving the vertical adjustment bracket 60 along the injector shaft 56. The vertical adjustment bracket 60 is moved until the spray nozzle 78 is a desired distance above the open mouth portion 274 of each sampling tube 186.

Once the injector is positioned as desired, the motor 112 is activated to rotate the disk shaft 128 and the disk 138 attached thereto. The speed or rpm of the motor 112 is controlled by the controller 123, as shown in FIG. 15. When the disk shaft 128 is rotated by the motor 112, the shaft encoder 160 generates a shaft position signal 300 as shown in FIG. 18. The shaft position signal 300 consists of a series of high values 302 and low values 304. Each high value 304 corresponds to one degree of rotation of the disk shaft 128, typically referred to as a crank angle. Therefore, 360 high values 302 occur for each complete rotation of the disk 138. Also shown in FIG. 18 is a second reference signal 306 produced by the shaft encoder 160. The second reference signal 306 includes a high value 308 which is generated each time a specific portion of the shaft completes a full rotation. Therefore, the high value 308, called the "top dead center", occurs once for each revolution of the disk 138. The combination of the shaft position signal 300 and the second reference signal 306 provides a source of timing to the controller 122.

As the disk 138 is rotating at a specific speed, the controller 122 generates an injector firing signal 310. Upon receiving the high value 312 of the injector firing signal 310, the injector 74 begins the injection process. The injector 74 will continue to pulse as long as the injector signal 310 remains high. Upon returning to the low value 314, the injector 74 will terminate its operation. Therefore, the injector firing signal 310 controls the timing of the start of injection, as well as the duration of the injector firing.

As the disk 138 rotates, the pair of shutters 178 act to block the spray opening 164 for a duration of time twice during each complete rotation of the disk 138. As shown in FIG. 5, the direction of rotation of the disk 138 is clockwise, as indicated by the arrow. In the preferred embodiment of the invention, each of the shutters 178 covers one-fourth of the disk 138. Therefore, each of the shutters consists of ninety crank angles and, when rotating, the disk 138 will cover the spray openings 164 for ninety crank angles, uncover the opening 164 for ninety crank angles, and again cover the opening 164 for ninety crank angles, and finally open the spray opening 164 for another ninety crank angles.

By knowing the position of each of the leading edges 176 on the disk 138 in relation to the top dead center signal 308, the controller 122 can fire the injector 74 a specific number of crank angles before the leading edge 176, and the following shutter 178, cover the spray opening 164. For example, if it is known that a leading edge 176 passes over the sampling tubes 186 of crank angle, after top dead center, the injector signal 310 can be generated a desired amount of crank angles before or after top dead center depending on how much spray is desired to reach the sampling tubes 186. Since the number of revolutions per minute of the disk 138 is known, each crank angle can be converted to a period of time. Therefore, the controller 122 can be used to determine the period of time at which the shutter 178 passes over spray opening 164 and the series of sampling tubes 186 as related to the time at which the injector 74 is fired.

The shutter 178 is shown passing over spray opening 164 in FIG. 7. As can be seen in the figure, the leading edge 176 cuts through the spray 82 and prevents any of the spray positioned above the shutter 178 at that time from reaching the series of sampling tubes 186. Therefore, the series of sampling tubes 186 measures the amount of spray a certain distance from the spray nozzle which reaches the collection tubes a selected amount of time after the start of injection. For example, FIG. 7 could represent the position of the shutter 178 3.1 msec after the beginning of injection, with the injector 74 positioned 3 cm above the sampling tubes 186. To get a measurable amount of liquid from the spray 82, the injector 74 is fired a series of times while maintaining the distance between the injector nozzle 78 and the series of collection tubes 86, as well as the particular timing between the shutter passing over the sampling tubes 186 and the beginning of injector firing.

In the particular example shown in FIG. 18, the injector signal 310 goes to the high value 312 causing the injector 74 to fire two crank angles 302 after the top dead center signal 308. Depending upon where the top dead center signal is generated with respect to one of the shutters 178, the shutter 178 will cut through the spray 82 a predetermined amount of time after the beginning of injection. To isolate larger or smaller portions of the spray 82, the relationship between the high value 312 of the injector signal 310 and the top dead center signal 308 is modified a number of crank angles 302.

Shown in FIG. 16 is a sample graph in which the vertical position of the injector is held constant with respect to the sampling tubes 186, while the time at which the shutter 178 isolates a portion of the spray to be measured is varied. As can be seen in the figure, 36% of the spray has reached the sampling tubes 3.37 millisecond after the beginning of injection. At this time period, the graph shows the volume of spray with respect to the distance in a plane normal to the injector axis. Also shown in FIG. 16 is the distribution of the spray at an infinite amount of time after the beginning of injection. This corresponds to the measuring device 10 being operated without the shutter mechanism 178. The single signal reading at an infinite time after the beginning of injection corresponds to a typical reading generated by a current steady state patternator. The reading shown in FIG. 16, however, is more accurate than the current steady state patternators since the collection tubes 185 include a gas relief opening 266 which reduces the stagnation pressure at the open mouth portion 274 of each sampling tube 186, which increases the accuracy of the reading.

Figure 17:
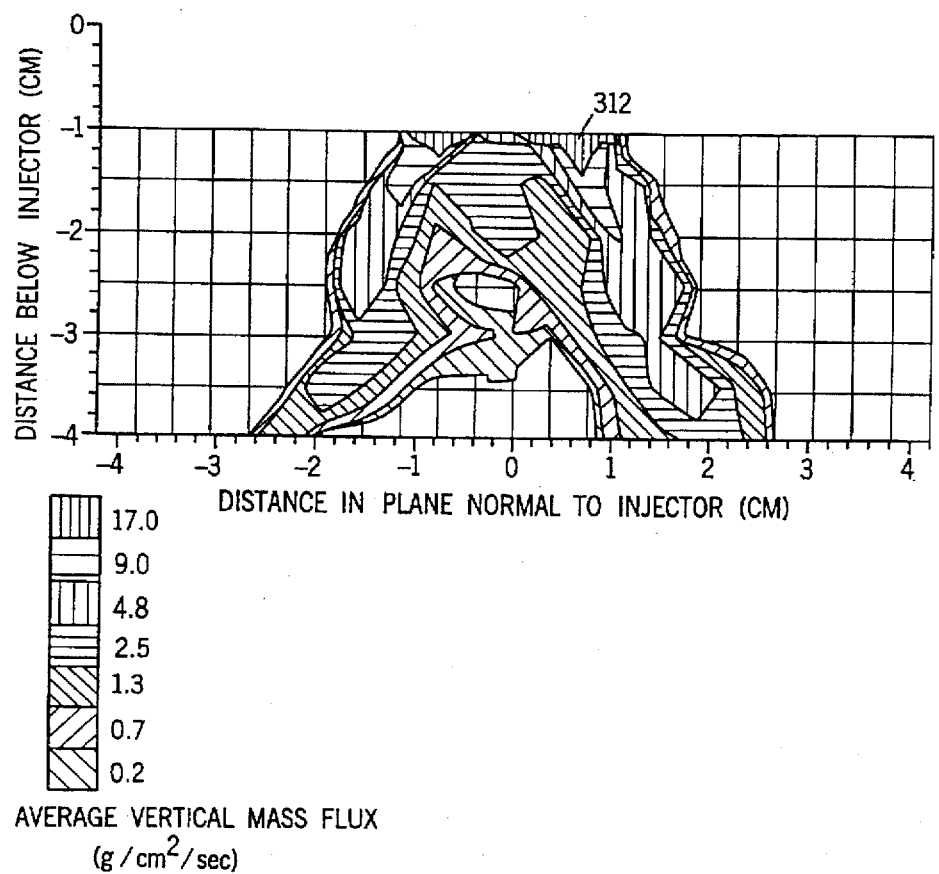

FIG. 17 shows a sample of the mass flux contours when the shutter isolates a portion of the spray a set time after the beginning of injection. In this sample graph, the injector nozzle was moved such that the distance between the injector 74 and the collection tubes 185 varied between one and four centimeters. As shown in the figure, measured data was obtained at points represented by the intersecting lines shown on the rectangular grid. Therefore, twenty-three individual sampling tubes were used, and measurements were taken at seven distances from the injection nozzle.

Specifically, the sample graph of FIG. 17 was generated as follows. With the injector 74 mounted 1 cm above the collection tubes 185, the shutter 178 was operated to isolate the spray 82 by passing over the collection tubes 185 3.37 msec after the start of the injector firing. Readings are then taken from each of the manometers 254 to determine the amount of mass collected during testing. This total mass is divided by the number of injections to determine the average mass per injection. The process is then repeated, with the shutter 178 now passing over the collection tubes 185 4.21 msec after the beginning of injection. Readings are again taken from each of the manometers 254 to determine the amount of mass collected during testing and the average mass per injection.

After testing at both 3.37 msec and 4.21 msec after the beginning of injection, the average mass per injection measured at 3.37 msec subtracted from the average mass per injection mass measured at 4.21 msec after the beginning of injection. This difference is divided by the product of the inner area of the open mouth 274 of the sample tube 186 and the time difference between measurements (0.91 msec) to determine the average mass flux per injection occurring 1 cm below the injector. The entire process previously described is repeated for additional distances below the injector nozzle 76. Each measured distance below the nozzle 76 is represented by a horizontal line in FIG. 17.

The period of time was determined by converting the number of crank angles between the firing of the injector 74 and shutter 178 passing over the collection tubes 185 into time.

The area of greatest liquid mass flux is represented by numeral 312. The lines shown in FIG. 17 represent decreasing amounts of mass flux as they move away from the area 312. The graph shown in FIG. 17 gives a detailed description of the average liquid mass flux in a spray at a variety of distances below the injector and outward from the spray axis.

Referring again to FIG. 18, the signal 314 represents the amount of light received by the receptor 277 shown in FIG. 9. As can be seen, the signal 314 is at a high level 316 until a short period of time after the injector is fired. As the particle droplets pass between the supply cable 276 and the receptor cable 277, the high signal 316 is reduced by the interference of the spray particles. The greater the amount of reduction 318 indicates larger droplets and/or a larger number of droplets or higher number density between the two optic fibers. In this manner, the signal 314 when combined with the average mass flux data provides an indication of the particle size and number density in the spray 82. Additionally, the amount of time between the beginning of the injector firing, as indicated by the beginning of high signal 312, and the beginning of the drop in signal 316 can be used to determine the spray velocity.

Although the invention has been described with a shutter 178 contained on the rotating disk 138, the inventors contemplate that any shutter mechanism 19 which can be operated to isolate a portion of the spray 82 a definite period of time after the start of injection firing would be an equivalent structure within the scope of the invention. The rotating disk 138 has been described in the preferred embodiment, since the disk 138 can be operated at a constant speed and the position of the shutter 178 accurately determined. The inventors contemplate a possible alternate embodiment, not shown, which uses a fast acting solenoid to operate a simple rectangular shutter which could isolate a portion of the spray 82 and block the remaining portion of the spray.

Referring again to FIG. 1, a strobe light 320 is shown positioned on the cover 162. The strobe light 320 can be connected to controller 122 and be time to flash at the instant the leading edge 176 of shutter 178 passes over the collection tubes 185. In this manner, the operator of the measuring device 10 can visually identify the portion of the spray being isolated by the shutter 178.

It is thought that the present invention and its advantages will be understood from the foregoing description and it will be apparent that various changes may be made thereto without departing from the spirit and scope of the invention and sacrificing all of its material advantages. The form herein before described being merely a preferred or exemplary embodiment thereof.

We claim:

1. A device for measuring the characteristics of a liquid spray pattern from a spray nozzle, the measuring device comprising:

a mounting platform for mounting a spray nozzle along a spray axis;

a collection means positioned below the mounting platform for collecting the spray from the nozzle;

a shutter mechanism operatively positioned below the mounting platform and above the collection means;

a controller in communication with the nozzle and the shutter mechanism, the controller operating the nozzle in timed relation to the shutter mechanism; and wherein the shutter mechanism selectively isolates a portion of the spray pattern such that only the isolated portion of the spray pattern reaches the collection means.

2. The measuring device of claim 1, wherein the injector platform is movable to selectively vary the distance between the mounting platform and the collection means.

3. The measuring device of claim 1, wherein the collection means comprises:

a plurality of collection tubes each having an open mouth portion to receive the spray from the spray nozzle and a reservoir for accumulating the received spray.

4. A device for measuring the characteristics of a spray pattern from a spray nozzle, the measuring device comprising:

a mounting platform for mounting a spray nozzle along a spray axis;

a collection means having a plurality of collection tubes arranged in a single row, the collection tubes each having an open mouth portion to receive the spray from the spray nozzle and a reservoir for accumulating the received spray, the collection means being positioned below the mounting platform for collecting the liquid spray from the nozzle;

a shutter mechanism operatively positioned below the mounting platform and above the collection means;

a controller in communication with the nozzle and the shutter mechanism, the controller operating the nozzle in timed relation to the shutter mechanism; and wherein the shutter mechanism selectively isolates a portion of the spray pattern such that only the isolated portion of the spray pattern reaches the collection means.

5. The measuring device of claim 4, wherein the single row of collection tubes are aligned normal to the spray axis.

6. The measuring device of claim 4, wherein the collection means further comprises:

a tube holder to securely position the plurality of collection tubes in the single row and provide desired spacing between adjacent tubes; and a translating stage for mounting the tube holder, the translating stage being movable in a direction normal to the spray axis to vary the position of the plurality of collection tubes.

7. The measuring device of claim 4, wherein each collection tube contains a gas relief opening positioned between the open mouth portion and the reservoir.

8. The measuring device of claim 4, further comprising a spray particle sizer mounted above the collection means to determine droplet size of the spray and spray velocity.

9. The measuring device of claim 8, wherein the spray particle sizer comprises a laser discriminator which generates an electronic signal corresponding to the size of the spray droplets entering the collection means.

10. A device for measuring the characteristics of a spray pattern from a spray nozzle, the measuring device comprising:

a mounting platform for mounting a spray nozzle along a spray axis;

a collection means positioned below the mounting platform for collecting the spray from the nozzle;

a shutter mechanism operatively positioned below the mounting platform and above the collection means, the shutter mechanism having a pair of open areas separated by a pair of solid shutters;

a controller in communication with the nozzle and the shutter mechanism, the controller operating the nozzle in timed relation to the shutter mechanism; and wherein the shutter mechanism selectively isolates a portion of the spray pattern such that only the isolated portion of the spray pattern reaches the collection means.

11. The measuring device of claim 10, wherein the pair of open areas and the pair of shutters are of equal length along the outer circumference of the circular disk.

12. The measuring device of claim 10, wherein each of the shutters have a leading edge, the leading edge having a tapered upper surface and a tapered lower surface.

13. The measuring device of claim 10, further comprising an encoder in communication with the controller to provide information concerning the position of the circular disk.

14. The measuring device of claim 10, further comprising a strobe light, the strobe light activating in a timed relation to the activation of the injector.

15. A method of measuring the characteristics of a spray pattern from a spray nozzle, the method comprising the steps of:

mounting a spray nozzle above a collection means such that a spray pattern may be emitted from the nozzle along a spray axis;

positioning a movable shutter mechanism between the spray nozzle and the collection means;

operating the shutter mechanism and the spray nozzle in timed relation to each other, such that the shutter mechanism operates to isolate a portion of the spray pattern;

controlling the amount of spray isolated by the shutter mechanism by monitoring the position of the shutter mechanism; generating a signal indicative of said position and activating the spray nozzle for a predetermined amount of time in response to said signal;

collecting the isolated portion of the spray pattern in the collection means; and measuring the portion of spray collected in the collection means.

16. The method of claim 15, further comprising the step of adjusting the distance between the spray nozzle and the collection means such that the mass flux can be measured at a selected distance from the spray nozzle.

17. The method of claim 15, wherein the shutter mechanism is a rotatable disk and the step of generating said signal is provided by an encoder which generates a signal corresponding to the rotational position of the disk.

18. The method of claim 17, wherein the injector is operated by the controller depending on the position of the disk, such that the shutter contained on the disk isolates a portion of the spray a selected amount of time after the injector is operated.

19. The method of claim 15, further comprising the step of measuring the size of the spray particles entering the collection means.

20. The method of claim 15, further comprising the step of measuring the velocity of the spray particles entering the collection means.

21. The method of claim 15, wherein the collection means comprises a plurality of collection tubes mounted in a single row positioned normal to the spray axis passing through the injector spray nozzle.

22. A device for measuring the characteristics of a liquid spray pattern from a spray nozzle, the measuring device comprising:

a movable mounting platform for securely mounting a spray nozzle along a spray axis;

a plurality of collection tubes each having an open mouth portion and a reservoir, the plurality of collection tubes being positioned below the mounting platform;

a shutter mechanism comprising a rotatable disk, the disk having at least one open area and at least one solid shutter, the shutter mechanism positioned below the injector platform and above the plurality of collection tubes;

a controller in communication with the spray nozzle and the shutter mechanism, the controller operating the spray nozzle in timed relation to the position of the shutter mechanism;

wherein the controller actuates the spray nozzle for a predetermined amount of time to release the liquid spray pattern based on the position of the rotating shutter mechanism such that the shutter mechanism selectively isolates a portion of the liquid spray pattern and only the isolated portion of the liquid spray pattern reaches the collection tubes.

23. The measuring device of claim 22, wherein the plurality of collection tubes are arranged in a single row aligned normal to the spray axis passing through the spray nozzle.

24. The measuring device of claim 23, wherein the single row of collection tubes are movable in a direction normal to the spray axis passing through the injector spray nozzle.

25. The measuring device of claim 22, wherein each of the collection tubes contains a gas relief opening positioned between the open mouth portion and the reservoir.

26. The measuring device of claim 22, further comprising a spray particle sizer mounted above the plurality of collection tubes to determine droplet size of the spray and spray velocity.

27. The measuring device of claim 26, wherein the spray particle sizer comprises a plurality of laser discriminators, each laser discriminator positioned above the open mouth of a corresponding collection tube, and each laser discriminator generates an electronic signal corresponding to the size of the spray droplets entering each of the collection tubes.

28. The measuring device of claim 22, wherein the circular disk has a pair of open areas separated by a pair of shutters, and the pair of open areas and the pair of shutters are of equal distance along the circumference of the circular disk.

29. The measuring device of claim 22, wherein the shutter has a leading edge having a tapered upper surface and a tapered lower surface.

30. The measuring device of claim 22, further comprising an encoder in communication with the controller to provide an electronic signal corresponding to the position of the rotating disk.

31. A method of measuring the characteristics of a spray pattern from an injector having a spray nozzle, the method comprising the steps of:
mounting a spray nozzle on a movable platform above a plurality of collection tubes;
positioning a rotating disk having at least one open area and at least one solid shutter between the spray nozzle and the plurality of collection tubes and along a spray axis;
generating an electronic signal corresponding to the position of the rotating disk;
generating an injector signal in a controller, such that the injector signal is generated based on the position of the rotating disk;
operating the injector upon the generation of the injector signal, such that the shutter contained on the rotating disk isolates a selected portion of the spray pattern;
collecting the isolated portion of the spray pattern in the plurality of collection tubes;
measuring the portion of spray collected in the collection tubes; and
moving the injector platform to adjust the distance between the injector and the collection tubes, such that a plurality of measurements can be made to determine the mass flux distribution in the spray pattern at a plurality of distances from the injector nozzle.

32. The method of claim 31, further comprises the step of eliminating the stagnation pressure at the open mouth of said collection tube by positioning a gas relief opening between the open mouth and the reservoir of the collection tubes.

33. A device for measuring the characteristics of a spray pattern from a spray nozzle, the measuring device comprising:
a movable mounting platform for securely mounting a spray nozzle along a spray axis;
a plurality of collection tubes arranged in a single row aligned normal to the spray axis passing through the spray nozzle, each collection tube having an open mouth portion and a reservoir, the plurality of collection tubes being positioned below the mounting platform;
a shutter mechanism comprising a rotatable disk, the disk having at least one open area and at least one solid shutter, the shutter mechanism positioned below the injector platform and above the plurality of collection tubes;
a controller in communication with the spray nozzle and the shutter mechanism, the controller operating the spray nozzle in time relation to the position of the shutter mechanism;
wherein the controller operates the spray nozzle in timed relation to the position of the rotating shutter mechanism such that the shutter mechanism selectively isolates a portion of a spray pattern and only the isolated portion of the spray pattern reaches the collection tube.

34. The measuring device of claim 33, wherein the single row of collection tubes are movable in a direction normal to the spray axis passing through the injector spray nozzle.

35. The measuring device of claim 33, further comprising an encoder in communication with the controller to provide an electronic signal corresponding to the position of the rotating disk.

36. A device for measuring the characteristics of a spray pattern from a spray nozzle, the measuring device comprising:
a movable mounting platform for securely mounting a spray nozzle along a spray axis,
a plurality of collection tubes each having an open mouth potion, a reservoir, and a gas relief opening positioned between the open mouth portion and the reservoir, the plurality of collection tubes being positioned below the mounting platform;
a shutter mechanism comprising a rotatable disk, the disk having at least one open area and at least one solid shutter, the shutter mechanism positioned below the injector platform and above the plurality of collection tubes;
a controller in communication with the spray nozzle and the shutter mechanism, the controller operating the spray nozzle in time relation to the position of the shutter mechanism;
wherein the controller operates the spray nozzle in timed relation to the position of the rotating shutter mechanism such that the shutter mechanism selectively isolates a portion of a spray pattern and only the isolated portion of the spray pattern reaches the collection tubes.

37. A device for measuring the characteristics of a spray pattern from a spray nozzle, the measuring device comprising:
a movable mounting platform for securely mounting a spray nozzle along a spray axis;
a plurality of collection tubes each having an open mouth portion and a reservoir, the plurality of collection tubes being positioned below the mounting platform;
a shutter mechanism comprising a rotatable disk, the disk having at least one open area and at least one solid shutter, the shutter mechanism positioned below the injector platform and above the plurality of collection tubes;

a controller in communication with the spray nozzle and the shutter mechanism, the controller operating the spray nozzle in time relation to the position of the shutter mechanism;

a spray particle sizer mounted above the plurality of collection tubes to determine droplet size of the spray and spray velocity, the spray particle sizer comprising a plurality of laser discriminators, each laser discriminator positioned above the open mouth of a corresponding collection tube, and each laser discriminator generating an electronic signal corresponding to the size of the spray droplets entering each of the collection tubes;

wherein the controller operates the spray nozzle in timed relation to the position of the rotating shutter mechanism such that the shutter mechanism selectively isolates a portion of a spray pattern and only the isolated portion of the spray pattern reaches the collection tubes.

38. A device for measuring the characteristics of a spray pattern from a spray nozzle, the measuring device comprising:

a movable mounting platform for securely mounting a spray nozzle along a spray axis;

a plurality of collection tubes each having an open mouth portion and a reservoir, the plurality of collection tubes being positioned below the mounting platform;

a shutter mechanism comprising a rotatable disk, the disk having a pair of open areas separated by a pair of shutters, the pair of open areas and the pair of shutters are of equal distance along the circumference of the disk, the shutter mechanism positioned below the injector platform and above the plurality of collection tubes;

a controller in communication with the spray nozzle and the shutter mechanism, the controller operating the spray nozzle in time relation to the position of the shutter mechanism;

wherein the controller operates the spray nozzle in timed relation to the position of the rotating shutter mechanism such that the shutter mechanism selectively isolates a portion of a spray pattern and only the isolated portion of the spray pattern reaches the collection tubes.

39. A device for measuring the characteristics of a spray pattern from a spray nozzle, the measuring device comprising:

a movable mounting platform for securely mounting a spray nozzle along a spray axis;

a plurality of collection tubes each having an open mouth portion and a reservoir, the plurality of collection tubes being positioned below the mounting platform;

a shutter mechanism comprising a rotatable disk, the disk having at least one open area and at least one solid shutter, the shutter having a leading edge having a tapered upper surface and a tapered lower surface, the shutter mechanism positioned below the injector platform and above the plurality of collection tubes;

a controller in communication with the spray nozzle and the shutter mechanism, the controller operating the spray nozzle in time relation to the position of the shutter mechanism;

the spray particle sizer comprises a plurality of laser discriminators, each laser discriminator positioned above the open mouth of a corresponding collection tube, and each laser discriminator generating an electronic signal corresponding to the size of the spray droplets entering each of the collection tubes;

wherein the controller operates the spray nozzle in timed relation to the position of the rotating shutter mechanism such that the shutter mechanism selectively isolates a portion of a spray pattern and only the isolated portion of the spray pattern reaches the collection tubes.

* * * * *